United States Patent

Suganuma

[11] Patent Number: 5,985,795
[45] Date of Patent: Nov. 16, 1999

[54] ANTIMICROBIAL COMPOSITION

[75] Inventor: Akio Suganuma, Side Plaza 203, 1-27-10, Saido, Urawa-shi, Saitama, Japan

[73] Assignees: Akio Suganuma, Urawa; Hitoshi Fujiwara, Sakura, both of Japan

[21] Appl. No.: 08/943,618

[22] Filed: Oct. 3, 1997

[30] Foreign Application Priority Data

Oct. 4, 1996 [JP] Japan .................................. 8-264139

[51] Int. Cl.⁶ .......................... A01N 43/52; A01N 43/80; A01N 47/04; A01N 47/30; A01N 59/16
[52] U.S. Cl. ............................................ 504/121; 424/405
[58] Field of Search ............................... 504/121; 424/405

[56] References Cited

U.S. PATENT DOCUMENTS

| | | | |
|---|---|---|---|
| 4,008,351 | 2/1977 | Inoue et al. | 428/411 |
| 4,163,020 | 7/1979 | Hagen et al. | 260/454 |
| 5,185,357 | 2/1993 | Inui | 514/372 |
| 5,622,546 | 4/1997 | Elbe et al. | 106/18.33 |

FOREIGN PATENT DOCUMENTS

| | | |
|---|---|---|
| 0 390 394 | 10/1990 | European Pat. Off. . |
| 0 680 695 | 11/1995 | European Pat. Off. . |
| 0 732 052 | 9/1996 | European Pat. Off. . |
| 7-76654 | 3/1995 | Japan . |
| 7 207 525 | 8/1995 | Japan . |
| 8-92012 | 4/1996 | Japan . |
| 1 389 940 | 4/1975 | United Kingdom . |
| 1 542 829 | 3/1979 | United Kingdom . |

OTHER PUBLICATIONS

Polymer incorporated synergistic fungicidal and algicidal compositions containing 2–(4–thiazolyl) benzimidazole and 2–octyl–4–isothiazolin–3–one, Chemical Abstracts, vol. 116, No. 1, Jan. 6, 1992, p. 236.
Abstract of JP 6–330,285, Nov. 1994.
Abstract of JP 9–208,413, Aug. 1997.

*Primary Examiner*—S. Mark Clardy
*Attorney, Agent, or Firm*—Flynn, Thiel, Boutell & Tanis, P.C.

[57] ABSTRACT

An antimicrobial composition which exhibits an excellent antimicrobial activity against various kinds of eumycetes, bacteria, actinomycetes, yeast and algae, is excellent in the quickness and persistency of the effect, and is extremely stable in itself. The antimicrobial composition contains an inorganic metal antimicrobial agent, a thiazole antimicrobial agent, a haloalkylthio antimicrobial agent, an imidazole antimicrobial agent, and a urea antimicrobial agent as the essential components.

17 Claims, 1 Drawing Sheet

ANTIMICROBIAL COMPOSITION

FIELD OF INVENTION

The present invention relates to an antimicrobial composition or mixture, more specifically to a composition exhibiting excellent antimicrobial and antiseptic activities against various kinds of eumycetes, bacteria, actinomycetes, yeast and algae.

BACKGROUND OF THE INVENTION

Antiblastic and antifungal agents have recently been used for the purpose of attaining clean, comfortable and healthy surroundings or for the purpose of inhibiting resources and articles from being deteriorated by microorganisms, and therefore have held an extremely important position in various articles and fields, for example, textiles, timbers, building materials, leathers, adhesives, metal working lubricants, rubbers, plastics, films, paper-pulp industry, cooling water, high-technology industry, electrical machinery and apparatus, optical instruments, air conditioners, stockbreeding, fishery, agriculture, forestry, drugs, agricultural chemicals, water, cosmetics, toiletries, sanitary goods, preservation of food, hospitals, homes for the aged, public institutions, household goods, sporting goods, school supplies, and toys.

Further, such antiblastic and antifungal agents have recently been required not only to be applicable to various fields as described above but also to be efficacious against various kinds of microorganisms. For example, it is expected to develop an antiblastic and antifungal agent capable of inhibiting the growth of all 57 kinds of microorganisms found in general architecture which were recognized by International Bio-Deterioration Symposium (Philadelphia, U.S.A.) in 1985 (at the sixth meeting held at Emanuel College, U.K.). Further, it is also expected to develop antiblastic, antifungal and antialgal agents capable of inhibiting the growth of not only eumycetes and bacteria but also algae.

In general, various inorganic metal compounds, organometallic compounds, organic compounds and natural products which have been used as antiblastic and antifungal agents each exhibit an inhibitory activity against several to ten-odd kinds of microorganisms. However, there has not been found any combination of two or more of these compounds which inhibits additional kinds of microorganisms beyond their respective inhibitory powers. Further, there were even cases wherein a combination of two or more of the above compounds only inhibited fewer kinds of microorganisms than the sum of the kinds of microorganisms which the compounds could inhibit individually.

Under these circumstances, in JP-A 8-92012, an antimicrobial composition was developed, which comprises a nitrile antimicrobial agent, a pyridine antimicrobial agent, a haloalkylthio antimicrobial agent, an organoiodine antimicrobial agent and a thiazole antimicrobial agent as the active ingredients and exhibits excellent antibacterial, antifungal and antialgal activities by virtue of the additivity and synergism of these agents. However, even this antimicrobial composition was not sufficiently satisfactory in its effect as an antimicrobial agent, such as the kinds of fungi which can be inhibited, of expression of antimicrobial power and persistency thereof, and other characteristics for antimicrobial agents, and in the stability of the composition in itself, and so on.

DISCLOSURE OF THE INVENTION

The inventors of the present invention have intensively studied to solve the above problems and have found that an antimicrobial composition which exhibits an excellent antimicrobial activity against various kinds of eumycetes, molds, bacteria, actinomycetes, yeast and algae, is excellent in quickness and persistency of the effect, and a high stability in itself, can be obtained by blending together an inorganic metal antimicrobial agent, a thiazole antimicrobial agent, a haloalkylthio antimicrobial agent, an imidazole antimicrobial agent and a urea antimicrobial agent.

Namely, the present invention relates to an antimicrobial composition characterized by comprising an inorganic metal antimicrobial agent, a thiazole antimicrobial agent, a haloalkylthio antimicrobial agent, an imidazole antimicrobial agent and a urea antimicrobial agent as the essential components.

The present invention provides an antifungal article or material comprising the composition defined above a and carrier.

The present invention provides a process for preventing the growth and activity of microorganisms by applying the composition as defined above to a locus where microorganisms will grow.

The present invention provides an antimicrobial composition comprising 1 to 96% by weight of the inorganic metal antimicrobial agent, 1 to 96% by weight of the thiazole antimicrobial agent, 1 to 96% by weight of the haloalkylthio antimicrobial agent, 1 to 96% by weight of the imidazole antimicrobial agent, and 1 to 96% by weight of the urea antimicrobial agent.

The present invention provides an antimicrobial composition comprising 38 to 58% by weight of the inorganic metal antimicrobial agent, 1 to 16% by weight of the thiazole antimicrobial agent, 2 to 22% by weight of the haloalkylthio antimicrobial agent, 3 to 23% by weight of the imidazole antimicrobial agent, and 11 to 31% by weight of the urea antimicrobial agent.

The antimicrobial composition of the present invention exhibits an excellent activity against a much larger number of kinds of microorganisms such as eumycetes, bacteria, actinomycetes, and yeast than conventional antimicrobial compositions. Further, the composition can exhibit an excellent activity against algae for the first time.

The antimicrobial composition of the present invention is excellent in persistency of the effect. It continues to be effective for a long time, even after new bacteria have come there.

The antimicrobial composition of the present invention exhibits an excellent activity, even if the concentration thereof is lower than that of conventional antimicrobial compositions.

The antimicrobial composition comprises plural kinds of antimicrobial agents so that a resistant bacteria may not be produced.

MODES FOR CARRYING OUT THE INVENTION

The antimicrobial composition of the present invention will now be described in detail.

The inorganic metal antimicrobial agent to be used for the antimicrobial composition of the present invention includes zeolite antimicrobial agents, zirconium phosphate antimicrobial agents, titania antimicrobial agents, glass antimicrobial agents, silver salt complexes, and soon. Among these agents, zirconium phosphate antimicrobial agents are preferable, zirconium phosphate-silver being particularly preferably used.

The thiazole antimicrobial agent to be used for the composition of the present invention includes isothiazolin-3-one compounds and benzothiazole compounds. Among these compounds, isothiazolin-3-one compounds are preferable.

The isothiazolin-3-one compounds include 1,2-benzisothiazolin-3-one, 2-(n-octyl)-4-isothiazolin-3-one, 5-chloro-2-methyl-4-isothiazolin-3-one, 2-methyl-4-isothiazolin-3-one, and 4,5-dichloro-2-cyclohexyl-4-isothiazolin-3-one. The benzothiazole compounds include 2-(4-thiocyanomethylthio)benzothiazole, 2-mercaptobenzothiazole sodium, and 2-mercaptobenzothiazole zinc. Among them, 1,2-benzisothiazolin-3-one is particularly preferable.

The haloalkylthio antimicrobial agent to be used for the composition of the present invention includes haloalkylthiophthalimide compounds, haloalkylthiotetrahydrophthalimide compounds, haloalkylthiosulfamide compounds, and haloalkylthiosulfimide compounds, among which haloalkylthiosulfimide compounds are preferable.

The haloalkylthiophthalimide compounds include N-fluorodichloromethylthiophthalimide and N-trichloromethylthiophthalimide; the haloalkylthiotetrahydrophthalimide compounds include N-1,1,2,2-tetrachloroethylthiotetrahydrophthalimide and N-trichloromethylthiotetrahydrophthalimide; the haloalkylthiosulfamide compounds include N-trichloro-methylthio-N-(phenyl)methylsulfamide, N-trichloro-methylthio-N-(4-chlorophenyl)methylsulfamide, N-(1-fluoro-1,1,2,2-tetrachloroethylthio)-N-(phenyl)methylsulfamide, and N-(1,1-difluoro-1,2,2-trichloroethylthio)-N-(phenyl)methylsulfamide; and the haloalkylthiosulfimide compounds include N,N-dimethyl-N'-phenyl-N'-(fluorodichloromethylthio)sulfimide, N,N-dichlorofluoromethylthio-N'-phenylsulfimide, and N,N-dimethyl-N'-(p-tolyl)-N'-(fluorodichloromethylthio) sulfimide. Among these compounds, N,N-dimethyl-N'-phenyl-N'-(fluorodichloromethylthio)-sulfamide is particularly preferable.

The imidazole antimicrobial agent to be used for the composition of the present invention includes benzimidazolecarbamic acid compounds, sulfur-containing benzimidazole compounds, and cyclic compounds of benzimidazole, among which cyclic compounds of benzimidazole are preferable.

The benzimidazolecarbamic acid compounds include methyl 2-benzimidazolecarbamate, methyl 1-butylcarbamoyl-2-benzimidazolecarbamate, methyl 6-benzoyl-2-benzimidazole-carbamate, and methyl 6-(2-thiophenecarbonyl)-2-benzimidazolecarbamate.

The sulfur-containing benzimidazole compounds include 2-thiocyanomethylthiobenzimidazole and 1-dimethylaminosulfonyl-2-cyano-4-bromo-6-trifluoromethylbenzimidazole.

The cyclic compounds of benzimidazole or benzimidazole compounds being substituted with another cyclic compound include 2-(4-thiazolyl)benzimidazole, 2-(2-chlorophenyl)-benzimidazole, 2-(1-(3,5-dimethylpyrazolyl))benzimidazole, and 2-(2-furyl)benzimidazole.

Among these compounds, 2-(4-thiazolyl)-benzimidazole is particularly preferable.

The urea antimicrobial agent to be used for the composition of the present invention includes halophenyl derivatives of dimethylurea, among which 3-(3,4-dichlorophenyl)-1,1-dimethylurea is preferable.

All of the above compounds are well-known ones and can readily be prepared by conventional processes. Further, many of them are commercially available, and such commercially available ones can also be used in the present invention.

The antimicrobial composition of the present invention can be prepared by mixing the above components together in suitable amounts, and the preferable amount of the composition to be added is 0.06 to 0.2% by weight based on the object of an article.

The form of the antimicrobial composition of the present invention is not particularly limited, but the composition may take various forms including water-based, powdery and solvent-based ones. That is, the above components are converted into a desirable form by the use of optional components generally used for the form, and applied to various articles and fields, for example, textiles, timbers, building materials, leathers, adhesives, metal working lubricants, rubbers, plastics, films, paper-pulp industry, cooling water, high-technology industry, electrical machinery and apparatus, optical instruments, air conditioners, stockbreeding, fishery, agriculture, forestry, drugs, agricultural chemicals, water, cosmetics, toiletries, sanitary goods, preservation of food, hospitals, homes for the aged, public institutions, household goods, sporting goods, school supplies, and toys.

The antimicrobial composition of the present invention is efficacious against various kinds of eumycetes, bacteria, actinomycetes, yeast and algae, specifically against not only 57 kinds of microorganisms found in general architecture which were recognized by International Bio-Deterioration Symposium (Philadelphia, U.S.A.), but also other microorganisms. Further, the composition has advantages by virtue of the effect due to the combination of inorganic and organic antimicrobial agents in that the antimicrobial spectrum is extremely broad, that the composition is extremely quick in its effect, and that the effect can persist for a long time.

The antimicrobial composition of the present invention is extremely stable in itself, and therefore has the following characteristics: ①the composition is free from lowering of activity or environmental pollution caused by the dissolution or volatilization of antimicrobial agents, because it comprises both an inorganic antimicrobial agent which is insoluble in aqueous media or organic solvents and organic antimicrobial agents which are insoluble in aqueous media; ②when the composition is incorporated into a plastic, film, sheet, cloth or synthetic paper, there occurs little change in the properties in the heating for molding or processing, so that the resulting product barely suffers from yellowing or lowering in the transparency; and ③when the composition is incorporated into a synthetic fiber, the resulting fiber is not affected by washing with an anionic detergent or the like.

Further, the antimicrobial composition of the present invention is freed from reductive discoloration which is one of the disadvantages of inorganic antimicrobial compositions, and is effective over a wide pH range. Further, the composition is composed of chemicals registered as existing chemical substances stipulated by the Ministry of International Trade and Industry and is therefore not problematic in safety.

EXAMPLES

Figure 1:
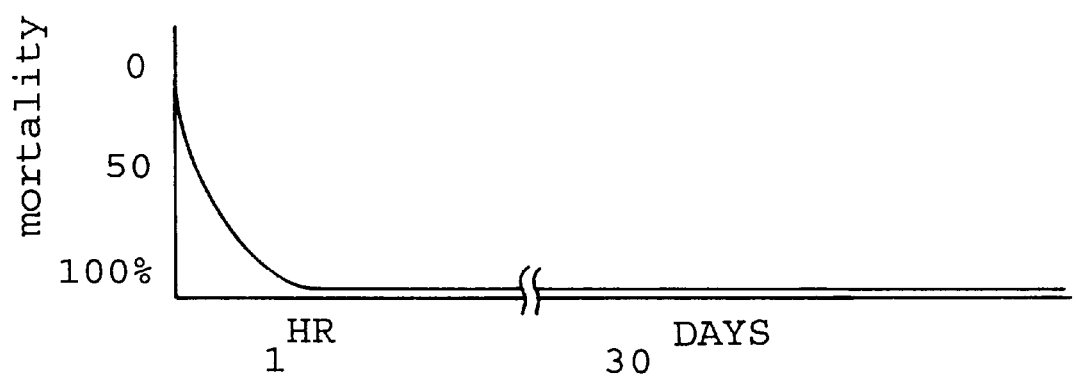
FIG. 1 is a graph showing the mortality of *Escherichia coli* as observed in Example 2 wherein the antimicrobial composition of the present invention was used.

The present invention will now be described in detail by referring to the following Examples, though the present invention is not limited to them.

Example 1

An antimicrobial composition was prepared by mixing together zirconium phosphate-silver as the inorganic metal antimicrobial agent, 1,2-benzisothiazolin-3-one as the thiazole antimicrobial agent, N,N-dimethyl-N'-phenyl-N'-(fluorodichloromethylthio)sulfamide as the haloalkylthio antimicrobial agent, 2-(4-thiazolyl)benzimidazole as the imidazole antimicrobial agent and 3-(3,4-dichlorophenyl)-1,1-dimethylurea as the urea antimicrobial agent in suitable amounts. An experiment was conducted to determine the minimum concentrations (ppm) of the antimicrobial composition at which the growth of the kinds of microorganisms which will be listed (including 57 kinds of microorganisms found in common buildings or living circumstances which were recognized by International Bio-Deterioration Symposium) was inhibited. More precisely, potato-agar media, Sabouraud's agar media and sucrose-agar media containing the above antimicrobial composition in various concentrations were prepared and test microorganisms of each kind prepared by single cell culture were planted on the media. The resulting media were kept in an incubator at 30° C. and a relative humidity of 95% for 7 days. The lowest concentration of the antimicrobial composition at which the test microorganisms did not grow was taken as the minimal inhibitory concentration (MIC value). MIC is a concentration per the medium. The MIC values of the kinds of microorganisms thus determined are as follows.

<<microorganisms having the MIC values of less than 1 ppm>>

| | |
|---|---|
| Tribonema sp. | Algae |
| Anacystis nidulans | Algae |
| Penicillium frequentance | Mold |
| Penicillium citrinum | Mold |
| Fusarium semitectum | Mold |
| Alternaria alternata | Mold |
| Eurotium tonophilum | Mold |
| Penicilium variable | Mold |
| Penicilium Purpurogenum | Mold |
| Aspergillus awamori | Mold |
| Blastomyces dermatidis | Yeast |
| Dactylium dendroides | Mold |
| Medurella mycetomii | Mold |
| Microsporum canis | Mold |
| Blastomyces italicum | Yeast |
| Rhizoctonia Violacea | Bacteria |
| Cerespora beticola | Mold |
| Cerespora musao | Mold |
| Claviceps purpurea | Mold |
| Colletotrichum trifolii | Mold |
| Penicillium glaucum | Mold |
| Pullularia pullans | Mold |
| Trichophyton mentagrophytes | Mold |
| Botrytis cinerea | Mold |
| Endothia paracitica | Bacteria |
| Sclerotina sclerotiorum | Bacteria |
| Venturia inaequalis | Bacteria |
| Penicillium roqueforti | Mold |
| Monilia laxa | Mold |
| Monilia fructigana | Mold |
| Lenzites trabea | Mold |
| Ceratocystis sp. | Mold |
| Diplodia viticola | Bacteria |
| Neurospora sitophilia | Mold |
| Oidium sp. | Mold |

<<microorganisms having the MIC values of at least 1 ppm and less than 10 ppm>>

| | |
|---|---|
| Aspergillus niger | Mold |
| Aspergillus oryzae | Mold |
| Aspergillus flavus | Mold |
| Aspergillus versicolor | Mold |
| Aspergillus fumigatus | Mold |
| Aspergillus nidulans | Mold |
| Aspergillus glaucus | Mold |
| Aspergillus terreus | Mold |
| Aspergillus phoenicus | Mold |
| Aspergillus tamari | Mold |
| Aspergillus wentii | Mold |
| Aspergillus restrictus | Mold |
| Aspergillus ochraceous | Mold |
| Chaetomium clivaceum | Mold |
| Chaetomium globosum | Mold |
| Cladosporium cladosporioides | Mold |
| Cladosporium sphaerospermum | Mold |
| Cladosporium herbarum | Mold |
| Bacillus cereus | Bacteria |
| Vibreo perahaemolyticus | Bacteria |
| Ascophyta pisi | Bacteria |
| Rhizoctonia solani | Bacteria |
| Alternaria pisi | Mold |
| Alternaria candidus | Mold |
| Trichophyton gypseum | Mold |
| Trichophyton rubrum | Mold |
| Penicillium luteum | Mold |
| Penicillium expansum | Mold |
| Phomosis citri | Mold |
| Diplodia natalensis | Mold |
| Fusarium oxysporum | Mold |
| Penicillium chrysogenum | Mold |
| Venticillium albo-atrum | Mold |
| Ustilago zeae | Mold |
| Penicillium citreo-viride | Mold |
| Oscillatoria aurea | Algae |
| Stichococcus bacillavis | Mold |
| Pestalotia neglecta | Mold |
| Fusarium roseum | Mold |
| Alternaria brassicicola | Mold |
| Geotrichum candidum | Mold |
| Geotrichum lactus | Mold |
| Gliocladium vireus | Mold |
| Phacidipycnus funfuracea | Mold |
| Phymatotricum omnivorum | Mold |
| Sclerotina fructincola | Mold |
| Aureobasidium pullulans | Mold |
| Fusarium solani | Mold |
| Penicillium notatum | Mold |
| Penicillium rubrum | Mold |
| Trichothecium roseum | Mold |
| Lenzites trabae | Mold |
| Monilia nigra | Mold |
| Microsporum audouini | Mold |
| Penicillium cyclopium | Mold |
| Colletotrichum lindemuthianum | Mold |
| Ceratocystis ulmi | Mold |
| Phoma terrestrius | Mold |
| Candida albicans | Yeast |
| Microsporum gypseum | Mold |
| Penicillium oxalicum | Mold |
| Penicillium spinulosum | Mold |
| Penicillium funiculosum | Mold |
| Penicillium digitatum | Mold |
| Fusarium roseum | Mold |
| Schizothrix sp. | Algae |
| Hormidium sp. | Algae |
| Ulothlichaceae sp. | Algae |

<<microorganisms having the MIC values of at least 10 ppm and less than 20 ppm>>

| | |
|---|---|
| Candida acutus | Yeast |
| Phaffia rhodozyma | Bacteria |
| Sporobolomyces roseus | Yeast |
| Pichia anomala | Bacteria |
| Pichia membranaefaciens | Bacteria |
| Zygosaccharomyces rouxii | Yeast |
| Zygosaccharomyces bailii | Yeast |
| Rhodotorula gulinis | Mold |
| Rhodotorula lactosa | Mold |
| Streptococcus lactis | Bacteria |
| Aerobacter aerogenes | Mold |
| Clostridium acetobutylicum | Mold |
| Clostridium sporogenes | Mold |
| Campylabacter jejuni | Bacteria |

-continued

| | |
|---|---|
| Cryptococcus lutealus | Mold |
| Schizosaccharomyces pombe | Yeast |
| Saccharomycodes ludwigii | Bacteria |
| Saccharomycodes pasteurianus | Mold |
| Pichia membranaefaciens | Mold |
| Debaryamyces hansenii | Bacteria |
| Hansemula anomala | Bacteria |
| Kloeckera apiculata | Bacteria |
| Candida utilis | Yeast |
| Aspergillus luchensis | Mold |
| Penicillium islandicum | Mold |
| Trichophyton ajelloi | Mold |
| Cryptococcus neoformans | Mold |
| Helminthosporium sp. | Mold |
| Rhizopus nigricans | Mold |
| Rhizopus oryzae | Mold |
| Hormoderdrum pedrosoi | Mold |
| Mucor racemosus | Mold |
| Sporotrichum schenckii | Mold |
| Stachybotrys sp. | Mold |
| Chlorella vulgaires | Algae |
| Epicoccum purpurascens | Mold |
| Pestalotia adusta | Mold |
| Penicillium nigricans | Mold |
| Penicillium lilacinum | Mold |
| Phoma glomerata | Mold |
| Paecilomyces lilacinus | Yeast |
| Cladosporium resinae | Mold |
| Gluconobacter suboxydans | Bacteria |
| Serratia maraesens | Bacteria |
| Micrococcus glatamicus | Bacteria |
| Streptococcus faecalis | Bacteria |
| Streptococcus thermophilus | Bacteria |
| Podiococcus soyae | Bacteria |
| Podiococcus acidilactici | Bacteria |
| Lactobacillus acidophilus | Bacteria |
| Lactobacillus plantarum | Bacteria |
| Autotrophic bacteria | Bacteria |
| Streptomyces griseus | Actinomycetes |
| Streptomyces aureofaciens | Actinomycetes |
| Streptomyces kasugaensis | Actinomycetes |
| Acuremonium charticola | Mold |
| Chlorococcum sp. | Algae |
| Oscilatoria sp. | Algae |

<<microorganisms having the MIC values of at least 20 ppm and less than 30 ppm>>

| | |
|---|---|
| Anabana sp. | Algae |
| Cladophora glomerata | Algae |
| Ankistrodemus angustus | Algae |
| Chlamydomonas reinhardii | Algae |
| Trentephohlia odarata | Algae |
| Alternaria tenuis | Mold |
| Cryptococcus albidas | Mold |
| Paecilomyces variotti | Yeast |
| Fusarium proliferatum | Mold |
| Anacystis sp. | Algae |
| Chlorella emersonii | Algae |

<<microorganisms having the MIC values of at least 30 ppm and less than 50 ppm>>

| | |
|---|---|
| Rhizopus storonifer | Mold |
| Escherichia coli | Bacteria |
| Staphylococcus aureus | Bacteria |
| Pseudomonas aeruginosa | Bacteria |
| Salmonella typhimurium | Bacteria |
| Legionella pneamophila | Bacteria |
| Leptospira interrogans | Bacteria |
| Rickettsia rickettsii | Bacteria |
| Mycobacterium tubercolosis | Bacteria |
| Proteus mirabilis | Bacteria |
| Proteus vulgaris | Bacteria |
| Staphylococcus epidermidis | Bacteria |
| Micrococcus candidus | Bacteria |
| Bacillus mycoides | Bacteria |
| Pseudomonas fluresceus | Bacteria |
| Bacillus subtillis | Bacteria |
| Bacillus megaterium | Bacteria |
| Streptoverticillum reticulum | Bacteria |
| Nigrospora oryazae | Mold |
| Trichoderma koningii | Mold |
| Trichoderma T-1 | Mold |
| Trichoderma viride | Mold |
| Fusarium moniliforme | Mold |
| Myrothecium verrucaria | Mold |
| Streptococcus faecalis | Bacteria |
| Salmonella enteritidis | Bacteria |
| Pseudomonas flourescens | Bacteria |
| Salmonella enterrica | Bacteria |
| Salmonella arizonae | Bacteria |
| Salmonella paratyphi | Bacteria |
| Salmonella choleraesuis | Bacteria |
| Campylobacter fetus | Bacteria |
| Streptococcus agalactiae | Bacteria |
| Serratia marcesceus | Bacteria |
| Serratia liguefaciens | Bacteria |
| Klebsiella oxytoca | Bacteria |
| Clostridium perfringens | Bacteria |
| Clostridium diffcile | Bacteria |
| Bacillus anthracis | Bacteria |
| Vibrio fluvialis | Bacteria |
| Vibrio mimicus | Bacteria |
| Vibrio ulnificus | Bacteria |
| Vibrio omma | Bacteria |
| Mucor mucedo | Mold |
| Mucor pusillus | Mold |
| Rhyzopus delemar | Mold |
| Absidia glauca | Mold |
| Pleurococcus sp. | Algae |
| Scytonema hofmannii | Algae |

<<microorganisms having the MIC values of at least 50 ppm and less than 70 ppm>>

| | |
|---|---|
| Wallemia sebi | Mold |
| Saccharomyces cerevisiae | Yeast |
| Klebsiella pneumoniae | Bacteria |
| Bacillus punctatum | Bacteria |
| Bacterium vulgaro | Bacteria |
| Bacterium pyocyaneum | Bacteria |
| Thio bacilus sp. | Bacteria |
| Fusarium nivale | Mold |
| Fusarium avenaceum | Mold |
| Fusarium acuminatum | Mold |
| Pythium vanterpoolii | Bacteria |
| Phyrarium cinereum | Bacteria |
| Aster yellows | Bacteria |
| Sugeran mosaic | Bacteria |
| Corticium fuciforme | Bacteria |
| Lepiota criststa | Bacteria |
| Lepiota castanae | Bacteria |
| Mesotaenium | Algae |
| Zygogonium | Algae |
| Trentephohlia aurea | Algae |

Example 2

The mortality of the antimicrobial composition used in Example 1 was determined by the use of *Escherichia coli*. Precisely, $4.6 \times 10^6$ of *Escherichia coli* was prepared and transplanted to a test piece made of polypropylene containing 0. 1% by weight of the antimicrobial composition described above, placed on a medium for the culture of *Escherichia coli*. The resulting system was cultured in a circulator (temp: 37° C., humidity: 95%) to determine the mortality. The results are shown in FIG. 1. It can be understood from the results shown in FIG. 1 that the antimicrobial composition of the present invention can destroy most (at least 99%) of *Escherichia coli* only in one hour and the effect can persist for 40 days or more without any change.

Example 3

The antiblastic test of the antimicrobial composition of the present invention used in Example 1 was determined by the use of *Staphylococcus aureus* as the test microorganism. Precisely, $1.1 \times 10^6$ of *Staphylococcus aureus* was prepared and transplanted to a test sample placed on a medium for the culture of *Pseudomonas aeruginosa*, and the resulting system was cultured in a circulator (temp: 37° C., humidity: 95%). The viable count was determined after 1, 24 and 48 hours and 30 days. The test samples used were test piece (Invention) produced by injection-molding a polypropylene containing 0.1% by weight of the antimicrobial composition used in Example 1 and test pieces produced by injection-molding a polypropylene free from the antimicrobial composition. The results are given in Table 1.

TABLE 1

|  | Viable count after one hour | Viable count after 24 hours | Viable count after 48 hours | Viable count after 30 days |
| --- | --- | --- | --- | --- |
| Compn.-free piece | $3.7 \times 10^7$ | $4.1 \times 10^8$ | $5.0 \times 10^8$ | $5.5 \times 10^8$ |
| Invention | $4.3 \times 10^3$ | $3.6 \times 10^3$ | $2.8 \times 10^3$ | $1.1 \times 10^2$ |

Example 4

The antimicrobial composition of the present invention used in Example 1 was examined for antifungal activity. Precisely, a test solution containing $10^6$ of 15 kinds of eumycetes was prepared and sprayed on a test sample placed on a Sabouraud's agar media (wet method). The resulting system was cultured in a circulator (temp: 28° C.±5° C., humidity: 90%±10%) to determine the fungal growth. The test samples used were test pieces (Invention) produced by injection-molding a polypropylene containing 0.1% by weight of the antimicrobial composition used in Example 1 and test pieces produced by injection-molding a polypropylene free from the antimicrobial composition. The results of the existence of the fungal growth observed after 10, 20 and 40 days are given in Table 2, wherein the symbol "+" means a case wherein fungi grew, and the symbol "−" a case wherein fungi did not grow.

TABLE 2

|  | after 10 days | after 20 days | after 40 days |
| --- | --- | --- | --- |
| Compn.-free piece | + | + | + |
| Invention | − | − | − |

Example 5

1) Preparation of an antimicrobial composition

An antimicrobial composition was prepared by mixing the five kinds of antimicrobial agent described in the following Table 3.

TABLE 3

| kind of antimicrobial agent | name of compound | content (wt. %) |
| --- | --- | --- |
| inorganic metal | zirconium phosphate-silver | 48 |
| thiazole | 1,2-benzisothiazolin-3-one | 6 |

TABLE 3-continued

| kind of antimicrobial agent | name of compound | content (wt. %) |
| --- | --- | --- |
| haloalkylthio | N,N-dimethyl-N'-phenyl-N'-(fluorodichloromethylthio)-sulfamide | 12 |
| imidazole | 2-(4-thiazolyl)benzimidazole | 13 |
| urea | 3-(3,4-dichlorophenyl)-1,1-dimethylurea | 21 |

2) Preparation of a test solution

The above antimicrobial composition was suspended in a sterilized saline solution in an amount of 1%. It was used as the test solution. Another sterilized saline solution free from the antimicrobial composition, was used as a control.

3) Preparation of a solution of fungi

*Staphylococcus aureus* IID 1677 resistant to methicillin (MRSA) was used as the test fungi. MRSA was shaken and cultured at 35° C. for 20 hours on an NB medium prepared by adding 0.2% of meat extract to a broth medium, prduced by Eiken Kagaku. The cultured medium was diluted 200 times by a sterilized phosphate-buffered saline solution. It was used as the solution of fungi.

4) Antimicrobial activity experiment 1 ml of the solution of fungi was added to 100 ml of the test solution and the control, and mixed. The resulting system was stored at 25° C. for 24 hours. The number of living strains was determined by drawing two lines in parallel of the bacteria with a platinum needle at 35° C. for 2days using SCDLPA agar media produced by Nihon Seiyaku. The results are shown in Table 4. It was confirmed that, with 1 ml of the test solution diluted ten times, the number of living strains could be determined by a preliminary test.

TABLE 4

| fungus | | the living number (/ml) | |
| --- | --- | --- | --- |
| | | starting time* | after 24 hours |
| MRSA | test solution | $1.2 \times 10^5$ | <10 |
| | control | $1.2 \times 10^5$ | $3.0 \times 10^3$ |

"<10" means no detection.
*The number of living strains (viable count) was determined in the control just after addition of the solution of fungi. This is the value of the starting time.

Example 6

1) Preparation of an antimicrobial composition

The antimicrobial composition prepared in Example 5 was used.

2) Preparation of a test solution

The test solution was prepared in the same manner as in Example 5, except that a sterilized purified water was used instead of a sterilized saline solution.

3) Preparation of a solution of fungi

*Escherichia coli* ATCC 43895 (colibacilli, serotype 0157:H7, species to produce Vero toxin I, II) was used as the test fungi. The solution of fungi was prepared in the same manner as in Example 5, except that a sterilized phosphate buffer was used instead of a sterilized phosphate-buffered saline solution.

4) Antimicrobial activity experiment

The antimicrobial activity experiment was carried out in the same manner as in Example 5. The results are shown in Table 5. It was confirmed that, with 1 ml of the test solution diluted ten times, the number of living strains could be determined by a preliminary test.

TABLE 5

| fungus | | the living number (/ml) | |
|---|---|---|---|
| | | starting time* | after 24 hours |
| colibacilli 0157:H7 | test solution | $3.0 \times 10^5$ | <10 |
| | control | $3.0 \times 10^5$ | $3.4 \times 10^5$ |

"<10" means no detection.
*The number of living strains was determined in the control just after addition of the solution of fungi. This is the value of the starting time.

I claim:

1. An antimicrobial composition comprising 1 to 96 wt. % of an inorganic metal antimicrobial agent selected from the group consisting of titania antimicrobial agents, glass antimicrobial agents and silver salt complexes, an isothiazolin-3-one antimicrobial agent in an amount of from 1 to 96 wt. % a halo-alkylthio antimicrobial agent in an amount of from 1 to 96 wt. %, an imidazole antimicrobial agent in an amount of from 1 to 96 wt. % and a urea antimicrobial agent in an amount of from 1 to 96 wt. %.

2. The composition as claimed in claim 1, wherein the inorganic metal antimicrobial agent is a titania antimicrobial agent.

3. The composition as claimed in claim 1, wherein the inorganic metal antimicrobial agent is a glass antimicrobial agent.

4. The composition as claimed in claim 1, wherein the inorganic metal antimicrobial agent is a silver salt complex.

5. An antimicrobial composition consisting essentially of 38–58 wt. % of zirconium phosphate-silver, 1–16 wt. % of 1,2-benzisothiazolin-3-one, 2–22 wt. % of N,N-dimethyl-N'-phenyl-N'-(fluorodichloromethylthio)sulfamide, 3–23 wt. % of 2-(4-thiazolyl)benzimidazole and 11–31 wt. % of 3-(3,4-dichlorophenyl)-1,1-dimethylurea.

6. An antimicrobial composition comprising a zirconium phosphate antimicrobial agent in an amount of from 1 to 96 wt. %, an isothiazolin-3-one antimicrobial agent in an amount of from 1 to 96 wt. %, a haloalkylthio antimicrobial agent in an amount of from 1 to 96 wt. %, an imidazole antimicrobial agent in an amount of from 1 to 96 wt. % and a urea antimicrobial agent in an amount of from 1 to 96 wt. %.

7. The composition as claimed in claim 6, wherein the haloalkylthio antimicrobial agent is a haloalkylthiosulfamide compound.

8. The composition as claimed in claim 6, wherein the imidazole antimicrobial agent is a cyclic compound of benzimidazole.

9. The composition as claimed in claim 6, wherein the urea antimicrobial agent is a halophenyl derivative of dimethylurea.

10. The composition as claimed in claim 6, wherein the inorganic metal antimicrobial agent, the thiazole antimicrobial agent, the haloalkylthio antimicrobial agent, the imidazole antimicrobial agent, and the urea antimicrobial agent are a zirconium phosphate antimicrobial agent, an isothiazolin-3-one compound, a haloalkylthiosulfamide compound, a cyclic compound of benzimidazole, and a halophenyl derivative of dimethylurea, respectively.

11. An antifungal article comprising the composition defined as claim 6 and a carrier.

12. The composition as claimed in claim 6, comprising 38 to 58% by weight of the inorganic metal antimicrobial agent, 1 to 16% by weight of the thiazole antimicrobial agent, 2 to 22% by weight of the haloalkylthio antimicrobial agent, 3 to 23% by weight of the imidazole antimicrobial agent, and 11 to 31% by weight of the urea antimicrobial agent.

13. The composition as claimed in claim 6, wherein the haloalkylthio antimicrobial agent is selected from the group consisting of haloalkylthiophthalimide compounds, haloalkylthiotetrahydrophthalimide compounds, haloalkylthiosulfamide compounds, and haloalkylthiosulfimide compounds.

14. The composition as claimed in claim 6, wherein the imidazole antimicrobial agent is selected from the group consisting of benzimidazolecarbamic acid compounds, sulfur-containing benzimidazole compounds, and cyclic compounds of benzimidazole.

15. A process for preventing the growth and activity of microorganisms by applying the composition as defined in claim 6 to a locus where microorganisms will grow.

16. The process of claim 15, wherein said locus is selected from the group consisting of textiles, timbers, building materials, leathers, adhesives, metal working lubricants, rubbers, plastics, films, paper-pulp industry, water, high-technology industry, electrical machinery and apparatus, optical instruments, air conditioners, stockbreeding, fishery, agriculture, forestry, drugs, agricultural chemicals, cosmetics, toiletries, sanitary goods, food, hospitals, homes for the aged, public institutions, household goods, sporting goods, school supplies and toys.

17. The process of claim 15, wherein said microorganism is selected from the group consisting of *Rhizopus oryzae, Rhizopus storonifer, Mucor mucedo, Mucor pusillus* and *Rhizopus delemar.*

* * * * *

UNITED STATES PATENT AND TRADEMARK OFFICE
CERTIFICATE OF CORRECTION

PATENT NO : 5 985 795
DATED : November 16, 1999
INVENTOR(S) : Akio SUGANUMA et al.

It is certified that error appears in the above-identified patent and that said Letters Patent is hereby corrected as shown below:

Column 11, Line 22    after "%" insert ---,---.

Signed and Sealed this

Fifth Day of December, 2000

Attest:

Q. TODD DICKINSON

Attesting Officer

Director of Patents and Trademarks